United States Patent [19]

Futagawa et al.

[11] Patent Number: 6,107,492
[45] Date of Patent: Aug. 22, 2000

[54] PROCESS FOR THE PREPARATION OF LEVETIRACETAM

[75] Inventors: Tooru Futagawa, Hyogo, Japan; Jean-Pierre Canvat, Brussels, Belgium; Emile Cavoy, Ham-Sur-Heure, Belgium; Michel Deleers, Linkebeek, Belgium; Michel Hamende, Uccle, Belgium; Vincent Zimmermann, Brussels, Belgium

[73] Assignees: UCB, S.A., Brussels, Belgium; Daicel Chemical Industries, Ltd., Tokyo, Japan

[21] Appl. No.: 09/306,988

[22] Filed: May 7, 1999

[30] Foreign Application Priority Data

May 8, 1998 [EP] European Pat. Off. ............ 98108430

[51] Int. Cl.$^7$ ..................... C07D 207/12; C07D 207/14; C07D 207/16
[52] U.S. Cl. ......................... 548/543; 548/546; 548/547; 548/550
[58] Field of Search .................................. 548/543, 546, 548/547, 550

[56] References Cited

U.S. PATENT DOCUMENTS

| | | | |
|---|---|---|---|
| 4,696,943 | 9/1987 | Gobert et al. | 514/424 |
| 4,861,872 | 8/1989 | Okamoto et al. | 536/18.7 |
| 4,912,205 | 3/1990 | Okamoto et al. | 536/20 |
| 5,518,625 | 5/1996 | Priegnitz et al. | 210/659 |
| 5,639,824 | 3/1990 | Yoshio Okamoto | 525/54.2 |

FOREIGN PATENT DOCUMENTS

| | | |
|---|---|---|
| 691582 | 9/1995 | Australia . |
| 0 157 365 | 10/1985 | European Pat. Off. . |
| 157365 | 10/1985 | European Pat. Off. . |
| 0 162 036 | 11/1985 | European Pat. Off. . |
| 0 471 082 | 2/1992 | European Pat. Off. . |
| 0 577 079 | 1/1994 | European Pat. Off. . |
| 0 706 982 | 4/1996 | European Pat. Off. . |
| 0 719 749 | 7/1996 | European Pat. Off. . |
| 2 225 322 | 5/1990 | United Kingdom . |
| 97/04011 | 10/1985 | WIPO . |
| 95/23125 | 8/1995 | WIPO . |
| 96/27615 | 9/1996 | WIPO . |

OTHER PUBLICATIONS

Franco et al., "3,5–Dimethylphenylcarbamates of amylose, chitosan and cellulos bonded on silica gel —Comparison of their chiral recognition abilities as high–performance liquid chromatography chiral stationary phases," J. of Chromatography A, 796, pp. 2, 1998.

Yashima et al., "3,5–Dimethylphenylcarbamates of cellulose and amylose regioselectively bonded to silica gel as chiral stationary phases for high–performance liquid chromatography," J. of Chromatography A, 877, pp. 11–19, 1994.

Patent Abstracts of Japan, vol. 095, No. 003, Apr. 28, 1995, & JP 06 343857 A (Daicel Chem. Ind. Ltd.), Dec. 20, 1994 *Abstract*.

Patent Abstracts of Japan, vol. 016, No. 443 (C–0985), Sep. 16, 1992 & JP 04 154795 A (Daicel Chem. Ind. Ltd.), May 27, 1992, *Abstract*.

Patent Abstracts of Japan, vol. 018, No. 001 (C–1148), Jan. 6, 1994 & JP 05 246950 A (Sumitomo Chem. Co. Ltd.), Sep. 24, 1993 *Abstract*.

*Primary Examiner*—Joseph Mckane
*Assistant Examiner*—James C. Oswecki
*Attorney, Agent, or Firm*—Wenderoth, Lind & Ponack, L.L.P.

[57] ABSTRACT

Levetiracetam is prepared by optical resolution of etiracetam by means of preparative high performance liquid chromatography or continuous simulated moving bed chromatographic system using silica gel supporting amylose tris(3, 5-dimethylphenylcarbamate) as a packing material.

12 Claims, No Drawings

PROCESS FOR THE PREPARATION OF LEVETIRACETAM

This invention relates to a process for preparing optically active alpha-ethyl-2-oxo-1-pyrrolidineacetamide (etiracetam). More particularly this invention relates to a commercial process for preparing (S) alpha-ethyl-2-oxo-1-pyrrolidineacetamide (levetiracetam) which is a compound useful for its protective activity against hypoxia and ischemia.

It is well known in the art that optical isomers of some pharmaceutical compounds having an asymmetric center may exhibit respectively different physiological activities. More specifically, one optical form of such a compound may be bioactive and the other inactive, inhibitory or toxic.

With respect to etiracetam it was disclosed in U.S. Pat. No. 4,696,943 that its laevorotatory enantiomer (levetiracetam) differs from its racemic mixture by (1) having a 10 times higher protective activity against hypoxia, and (2) having a 4 times higher protective activity against ischemia.

According to the same document, (S)-alpha-ethyl-2-oxo-1-pyrrolidineacetamide can be prepared by one or the other of the two following processes:

(a) reacting (S)-alpha-ethyl-2-oxo-1-pyrrolidineacetic acid successively with (1) and alkylhaloformate and with (2) ammonia;

(b) cyclizing an (S)-2-amino-butanamide.

The former process however is somewhat awkward to carry out, since the reaction is generally implemented at a temperature between −10° and −60° C. and, hence the thermal profile is difficult to control in the reactor when operating on a large scale. The latter process also presents a major drawback resulting from the fact that the alkyl (S)-4 [[1-(aminocarbonyl)propyl]amino]-butyrate or (S)-N-[1-(aminocarbonyl)propyl]-4-halobutanamide required for cyclization is not easily available, being itself prepared by the reaction of condensing (S)-2-aminobutanamide with either an alkyl 4-halobutyrate or a 4-halobutyryl halide.

U.S. Pat. No. 4,696,943 mentions that levetiracetam cannot be directly obtained from the racemate by separation of the two enantiomers. U.S. Pat. No. 4,696,943 additionally discloses levetiracetam with melting points from 115 to 118° C. and $[\alpha]_D^{25}$ from −89.7° to −91.3°.

British patent No. 2,225,322 further discloses a process wherein (S)-alpha-ethyl-2-oxo-1-pyrrolidine-acetamide is prepared by hydrogenolysis of (S)-alpha-[2-(methylthio) ethyl]-2-oxo-1-pyrrolidineacetamide by means of a desulphurizing agent such as Raney nickel or $NaBH_4$/$NiCl_2.6H_2O$. Again such a process is not easy to control on a large scale, being generally carried out in water at a temperature between 50° and 100° C., hence requiring specific reactor equipment and handling precautions.

Consequently there is a need for designing a new process for preparing (S)-alpha-ethyl-2-oxo-1-pyrrolidineacetamide which would be free of the various disadvantages of the hitherto known processes mentioned above. On the other hand, chiral chromatography is well known as a useful means for the separation of pharmaceutical compounds. However although chiral chromatography is widely spread as an analytical technique, the number of technical criteria required for its applicability on an industrial scale makes it difficult to select its appropriate design parameters for the mass production of a specific pharmaceutical compound.

EP-A-157,365 discloses, in its example 2, resolving amide racemates by treatment with amylose trisphenylcarbamate while using a hexane/2-propanol (9:1) mixture as the eluent.

Under these circumstances, a commercial process by which the laevorotatory enantiomer of alpha-ethyl-2-oxo-1-pyrrolidineacetamide can be isolated by chiral chromatography is strongly desired.

The main expected advantage of such a process over the previously known processes would be the fact of starting from etiracetam which can be easily prepared by a process such as disclosed in British Pat. No 1,309,692.

Different chromatographic processes for separating enantiomers of chemical compounds are already known in the art. In particular it is already known from U.S. Pat. No. 5,126,055 a process for separating optical isomers in a simulated moving bed, which allows an optical isomer mixture to be separated continuously and efficiently while using a reduced amount of desorbing liquid, and which can deal with a large amount of optical isomers. The same document discloses the separation of 1,3-butanediol diacetate while using Chiralcel OB of 20 $\mu$m particle diameter as the optical resolution packing and a 9:1 hexane/isopropanol mixture as the desorbing liquid. It also discloses the separation of α-phenylethyl alcohol while using Chiralcel OB of 30–50 $\mu$m particle diameter as the optical resolution packing. As is known in the art, Chiralcel OB is a silica gel supporting cellulose benzoyl ester available from Daicel Chemical Industries (Japan).

In U.S. Pat. No. 5,456,825 there is also disclosed an improved simulated moving bed separation system according to which a 1-phenyl ethyl alcohol optical isomer mixture is resolved while using Chiralcel OD of 20 $\mu$m particle diameter as the optical resolution packing and a 9:1 hexane/isopropanol mixture as the desorbing liquid. As is known in the art, Chiralcel OD is a silica gel supporting cellulose tris-(3,5-dimethyl phenyl carbamate) available from Daicel Chemical Industries (Japan).

It is known from International Patent application WO 95-23125 a process for preparing optically active mevalonolacton compounds by means of simulated moving bed chromatography using columns filled with a filler for optical resolution such as various Chiralcel fillers available from Daicel Chemical Industries (Japan). It is also known from EP-A-719,749 a process for separating optical isomers in a simulated moving bed system while using a packing, such as a packing sold under the trademark Chiralpak AD, having an average particle size of 1 to 100 $\mu$m.

Now it is an objective of the present invention to provide an efficient process for the preparation of (S)-α-ethyl-2-oxo-1-pyrrolidineacetamide by means of chromatography, the term "efficient" being defined here as meaning that the said process is able to provide a good combination of selectivity and resolution which leads to productivity, whereas chiral chromatography generally provides an improvement of selectivity only at the expense of productivity and vice-versa.

The present invention is based on the surprising and unexpected discovery that silica gel supporting amylose tris(3,5-dimethylphenylcarbamate), an optical resolution filler available from Daicel Chemical Industries (Japan) under the tradename Chiralpak AD or a chemically modified form thereof, provides the best efficiency for resolving an optical isomer mixture of α-ethyl-2-oxo-1-pyrrolidine acetamide and thus for preparing levetiracetam with a purity which is satisfactory for its use as a pharmaceutical active ingredient.

Thus the present invention relates to a process for the preparation of levetiracetam wherein optical resolution of racemic α-ethyl-2-oxo-1-pyrrolidine acetamide is performed by means of a preparative high performance liquid chromatography or continuous simulated moving bed chromatographic system which uses at least one column packed with an optical resolution packing material wherein said packing material consists of silica gel supporting amylose tris(3,5-dimethylphenylcarbamate) or a chemically modified form thereof. Typically the efficiency of this process is related to the interactions between etiracetam and the filler that lead to separation performances measured by the volume ratio k', the separation coefficient or selectivity α and the separation degree or resolution $R_s$.

According to one embodiment of the present invention, the process is carried out by means of a simulated moving bed system, the definition of which is well accepted in the art and is provided, for example, in JP-B-15681/1967. In addition EP-A-719.749 provides an improved simulated moving bed system which can also be used in the process of the invention.

Although the average particle diameter of the packing material varies depending on the volume flow rate of the solvent flowing in the simulated moving bed, it is usually 1 to 300 μm, preferably 2 to 100 μm, more preferably 5 to 75 μm and most preferably 10 to 30 μm. As is known in the art, the selection of the average particle diameter of the packing material will help regulating the pressure drop in the simulated moving bed and the number of theoretical adsorption plates. The particles of the packing material may be poreless but is it preferred that they are porous. The pore diameter of the porous particles is usually 10Å–5,000 Å, preferably 200 Å–2,000 Å.

The amount of the amylose tris(3,5-dimethylphenylcarbamate) or chemically modified form thereof is usually 1–99 wt % of the amount of the silica gel support, preferably 5–50 wt %.

In this embodiment of the invention, the eluents to be fed to the simulated moving bed system include, for example, organic solvents such as alcohols, e.g. ethanol, and aliphatic and alicyclic hydrocarbons, e.g. heptane, cyclohexane, pentane and their mixtures. A preferred eluent consists of a mixture comprising about 5–100 volume % ethanol, about 0–95 volume % heptane and not more than about 4 volume % water. A more preferred eluent system comprises 40–65% (volume) ethanol, 30–60 volume % heptane and not more than 2% (volume) water. Additionally the process of the invention should preferably be performed at a temperature of about 5–50° C., more preferably 15–40° C.

While performing the process of the invention in the manner described hereinabove, it is possible to obtain (S)-alpha-ethyl-2-oxo-1-pyrrolidineacetamide with a chiral chromatography purity not less than 96% and preferably not less than 98%.

Now the invention will be described by reference to the following embodiments, which should not be understood as limiting its scope.

EXAMPLE 1

Terms used hereinafter are defined as follows:

| | |
|---|---|
| dead time | $t_0$ = retention time of a non retained compound such as 1,3,5-tri-tert.-butylbenzene |
| Volume ratio | k' = {(retention time of antipode) - dead time)}/(dead time) |
| Separation coefficient | α = (volume ratio of strongly-adsorbed antipode)/(volume ratio of weakly-adsorbed antipode) |
| Separation degree | $R_s$ = 2 × (distance between peaks of strongly-adsorbed antipode and weakly-adsorbed antipode)/(sum of bands of two peaks) |

When a chromatographic column is equilibrated with a given solvent, during at least three hours before starting the following experiments, injection of 10 μl of a 1 g/l racemic mixture of etiracetam dissolved in the above eluent is injected onto the column under the conditions described hereinafter.

Using a column 0.46 cm in inner diameter and 25 cm in length filled with 10 μm silica gel supporting amylose tris(3,5-dimethylphenylcarbamate) (CHIRALPAK AD marketed by Daicel Chemical Industries, Japan) the laevorotatory and dextrorotatary enantiomers of etiracetam were optically separated under a fixed flow of 1 ml/1 min. and at a temperature of 30° C. Conditions of chromatography (eluent composition), volume ratios $k'_1$ and $k'_2$ of both enantiomers, separation coefficient and separation degree are indicated in the Table below:

TABLE

| Eluent (% volume) | $k'_1$ | $k'_2$ | α | $R_s$ |
|---|---|---|---|---|
| Ethanol (50)/heptane (50) | 0.435 | 0.934 | 2.149 | 4.138 |
| Ethanol (60)/heptane (40) | 0.346 | 0.731 | 2.113 | 3.847 |
| Ethanol (50)/cyclohexane (50) | 0.290 | 0.750 | 2.584 | 5.490 |
| Ethanol (60)/cyclohexane (40) | 0.249 | 0.614 | 2.469 | 4.856 |
| Ethanol (50)/octane (50) | 0.417 | 0.877 | 2.105 | 4.683 |
| Ethanol (60)/octane (40) | 0.337 | 0.693 | 2.058 | 4.105 |
| Ethanol (50)/isooctane (50) | 0.421 | 0.857 | 2.036 | 5.144 |
| Ethanol (50)/dodecane (50) | 0.413 | 0.852 | 2.058 | 4.774 |
| Ethanol (50)/hexane (50) | 0.399 | 0.891 | 2.234 | 6.227 |
| Ethanol (60)/hexane (40) | 0.325 | 0.701 | 2.160 | 5.337 |
| Ethanol (50)/methylcyclohexane (50) | 0.294 | 0.704 | 2.394 | 4.396 |
| Ethanol (50)/pentane (50) | 1.006 | 1.764 | 1.754 | 7.500 |

EXAMPLE 2

A simulated moving bed system is used, which comprises a plurality of columns filled with silica gel supporting amylose tris(3,5-dimethylphenylcarbamate) and serially arranged to form a flow circuit. The fluid flows only in one direction.

In this simulated moving bed, an inlet port for an eluent; an outlet port through which a solution containing an optical isomer easily adsorbable by the filler (extract) is taken out; an inlet port through which a solution containing racemic etiracetam is introduced; and an outlet port through which a solution containing an optical isomer not easily adsorbed by the filler (raffinate) is taken out are assigned in this order in the direction of fluid flow; and the working positions of these ports are intermittently and successively shifted in the direction of fluid flow.

Separation by adsorption of etiracetam in the simulated moving bed chromatographic process is basically effected by continuously and cyclically carrying out the adsorption step, the concentration step, the desorption step and the eluent recovery step as follows:

(1) Adsorption step

Racemic etiracetam is contacted with the optical resolution filler, whereby an optical isomer which is easily adsorbed by the filler (extract) is adsorbed, and another optical isomer which is not easily adsorbed by the filler (the raffinate) is recovered together with the eluent.

(2) Concentration step

The optical resolution filler which has adsorbed the extract is contacted with a portion of the extract described at step (3) below and the raffinate which is retained on the optical resolution filler is expelled and thus the extract is concentrated.

(3) Desorption step

The optical resolution filler which has adsorbed the extract is contacted with the eluent, the extract is expelled from the filler and taken out of the simulating moving bed together with the eluent as extract.

(4) Eluent recovery step

The optical resolution filler which contains substantially the eluent only is contracted with a portion of the raffinate (i.e. that part containing the optical isomer which is an antipode of the isomer contained in the extract) and a portion of the eluent contained in the optical resolution filler is recovered as an eluent recovery.

While performing the above-described process for the separation of etiracetam, suitable separation coefficient and productivity can be achieved when the eluent is a mixture of 60% (vol.) ethanol and 40% (vol.) heptane).

What is claimed is:

1. A process for preparing levetiracetam, which comprises:

passing a racemic mixture of alpha-ethyl-2-oxo-1-pyrrolidine acetamide through at least one chromatographic column packed with an optical resolution packing material, wherein said packing material consists of silica gel supporting amylose tris(3,5-dimethylphenylcarbamate) or a chemically modified form thereof, to optically resolve levetiracetam from the racemic mixture.

2. A process according to claim 1, wherein the racemic mixture is passed through a preparative high performance liquid chromotoaphy system.

3. A process according to claim 1, wherein the racemic mixture is passed through a continuous simulated moving bed chromatography system.

4. A process according to claim 1, wherein the average particle diameter of the packing material is 1 to 300 μm.

5. A process according to claim 1, wherein the particles of the packing material are porous.

6. A process according to claim 5, wherein the pore diameter of the particles is 10 Å–5000 Å.

7. A process according to claim 1, wherein the amylose tris(3,5-dimethylphenylcarbamate) or chemically modified form thereof is 1 to 99% weight percent of the silica gel support.

8. A process according to claim 1, wherein the eluent to be fed to the chromatography column contains at least one member selected from the group consisting of alcohols, hydrocarbons and their mixtures.

9. A process according to claim 8, wherein the eluent is a mixture comprising 5–100 volume percent ethanol, 0–95 volume percent heptane and not more than 4 volume percent water.

10. A process according to claim 1, wherein the process is performed at a temperature of 5–50° C.

11. A process according to claim 4, wherein the average particle diameter of the packing material is 10 to 30 μm.

12. A process according to claim 8, wherein the eluent mixture comprises 40–65% by volume of ethanol, 30–60% by volume of heptane and not more than 2% by volume of water.

* * * * *